United States Patent [19]

Passerini et al.

[11] 4,001,424
[45] Jan. 4, 1977

[54] 1-OXO-1H-NAPHTHO [2,1-B] PYRAN DERIVATIVES FOR TREATING DEPRESSION

[75] Inventors: Norina Passerini, Milan; Aldo Ermili, Genoa; Giorgio Roma, Genoa; Alessandro Balbi, Genoa; Mauro Mazzei, Genoa, all of Italy

[73] Assignee: Carlo Erba, S.p.A., Italy

[22] Filed: Mar. 12, 1976

[21] Appl. No.: 666,329

Related U.S. Application Data

[62] Division of Ser. No. 493,611, July 31, 1974, abandoned.

[30] Foreign Application Priority Data

Sept. 27, 1973  Italy ................................ 29430/73
Sept. 28, 1973  Italy ................................ 29485/73

[52] U.S. Cl. ........................... 424/283; 260/345.2
[51] Int. Cl.$^2$ ...................................... A61K 31/35
[58] Field of Search ................ 260/345.2; 424/283

[56] References Cited
OTHER PUBLICATIONS

Ermili et al., Gazz. Chim.; Ital., 101, 269 (1971).
Ermili et al., Gazz. Chim.; Ital., 101, 651, (1971).
Rubin et al., J. Pharmacol., 120, 125, (1957).

*Primary Examiner*—Stanley J. Friedman
*Attorney, Agent, or Firm*—Murray and Whisenhunt

[57] ABSTRACT

1-Oxo-1H-naphtho [2,1-b] pyran derivatives, such as, for instance, 1-oxo-3-(N-methyl-N-ethyl) amino-1H-naphtho [2,1-b] pyran, are disclosed, as well as pharmaceutical compositions containing same and the method of treating depression by administering such compositions.

These compounds are active on the central nervous system, and therefore function as antidepressive agents.

7 Claims, No Drawings

1-OXO-1H-NAPHTHO [2,1-b] PYRAN DERIVATIVES FOR TREATING DEPRESSION

This is a division of application Ser. No. 493,611 filed July 31, 1974 now abandoned.

THE PRESENT INVENTION relates to 1-oxo-1H-naphtho[2,1-b]pyran derivatives, a process for their preparation and pharmaceutical compositions containing them.

An object of the present invention is represented by new 1-oxo-1H-naphtho [2,1-b]pyran derivatives having the following general formula:

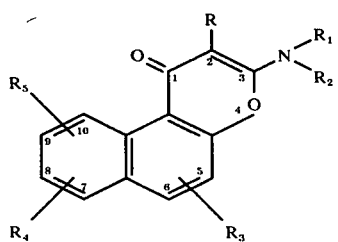

wherein R may be hydrogen, halogen or $C_1$-$C_6$ alkyl; each of the $R_3$, $R_4$ and $R_5$ groups, being the same or different, may be hydrogen, halogen, nitro, hydroxy, amino, $C_1$-$C_6$ alkyl, $C_1$-$C_6$ alkoxy or trifluoromethyl; each of the $R_1$ and $R_2$ groups, being the same or different, may be hydrogen, $C_1$-$C_6$ alkyl, $C_2$-$C_6$ alkenyl, or $R_1$ and $R_2$, taken together with the nitrogen atom, may form a monocyclic ring which may contain one or more other heteroatoms, under the condition that, when both R and $R_3$, $R_4$, $R_5$ are hydrogen, $R_1$ and $R_2$ cannot be both methyl or both ethyl or both propyl, and not even can they be, taken together with the nitrogen atom, the N-pyrrolidinyl or the N-piperidyl radical; as well as pharmaceutically acceptable salts of the compounds of formula (I).

When $R_1$ and $R_2$, taken together with the nitrogen atom, form a heteromonocyclic ring, said ring is preferably azacycloheptyl or, when at least one of R, $R_3$, $R_4$, $R_5$, is different from hydrogen, said heteromonocyclic ring may also be the N-pyrrolidinyl or the N-piperidyl radical.

Another object of the present invention is represented by pharmaceutical compositions containing a suitable carrier and, as an active principle, a compound of formula (I) of a salt thereof, wherein R, $R_3$, $R_4$ and $R_5$ are as hereabove defined, and wherein $R_1$ and $R_2$ may be not only defined as hereabove indicated, but also, even when both R and $R_3$, $R_4$, $R_5$ are hydrogen, they may be both methyl or both ethyl or both propyl or, taken together with the nitrogen atom, they may be the N-pyrrolidinyl or the N-piperidyl radical.

The alkyl and alkoxy groups may be branched or straight chain. Preferred compounds and, respectively, preferred active ingredients of the pharmaceutical compositions of the present invention are those wherein R, $R_3$, $R_4$ and $R_5$ are hydrogen atoms, and wherein $R_1$ and $R_2$, being the same or different, are $C_1$-$C_6$ alkyl groups, or, $R_1$ is hydrogen and $R_2$ is a $C_1$-$C_6$ alkyl.

When $R_1$ and/or $R_2$ are $C_1$-$C_6$ alkyl groups, said alkyl groups are preferably methyl and/or ethyl.

Examples of pharmaceutically acceptable salts are those with hydrochloric, citric and tartaric acid.

Specific examples of compounds object of the present invention, or respectively, specific active principles of the pharmaceutical compositions of this invention are:

1-oxo-3-(N-methyl-N-ethyl) amino-1H-naphtho[2,1-b]pyran;
1-oxo-3-methylamino-1H-naphtho [2,1-b]pyran;
1-oxo-3-ethylamino-1H-naphtho-[2,1-b]pyran;
1-oxo-3-propylamino-1H-naphtho[2,1-b]pyran;
1-oxo-3-isopropylamino-1H-naphtho[2,1-b]pyran;
1-oxo-3-diisopropylamino-1H-naphtho-[2,1-b]pyran;
1-oxo-3-diallylamino-1H-naphtho[2,1-b]pyran;
1-oxo-3-diethylamino-9-methoxy-1H-naphtho[2,1-b]pyran;
1-oxo-3-diethylamino-5-methoxy-1H-naphtho[2,1-b]pyran;
1-oxo-2-chloro-3-diethylamino-1H-naphtho[2,1-b]pyran;
1-oxo-2-bromo-3-diethylamino-1H-naphtho[2,1-b]pyran;
1-oxo-2-chloro-3-(N-methyl-N-ethyl) amino-1H-naphtho[2,1-b]pyran;
1-oxo-2-bromo-3-(N-methyl-N-ethyl) amino-1H-naphtho[2,1-b]pyran;
1-oxo-2-methyl-3-diethylamino-1H-naphtho[2,1-b]pyran;
1-oxo-3-dimethylamino-1H-naphtho[2,1-b]pyran;
1-oxo-3-diethylamino-1H-naphtho-[2,1-b]pyran;
1-oxo-3-dipropylamino-1H-naphtho-8 2,1-b]pyran;
1-oxo-3-(N-pyrrolidinyl)-1H-naptho[2,1-b]pyran;
1-oxo-3-(N-piperidyl)-1H-nphtho[2,1-b]pyran.

The new 1-oxo-1H-naphtho[2,1-b]pyran derivatives can be prepared by reacting a compound of general formula

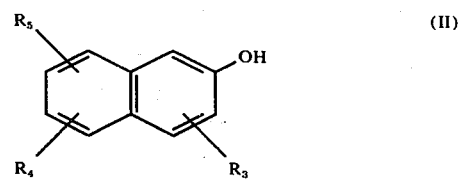

wherein $R_3$, $R_4$ and $R_5$ are as hereabove defined, with a compound of general formula

wherein $R_1$ and $R_2$ are as hereabove defined, R' is an alkyl and R'' is a hydrogen or a halogen atom, and by subsequent hydrolysis to obtain the compounds of formula (I) wherein R is hydrogen or halogen, and subsequently, if desired, by converting a compound of formula (I) wherein R is a hydrogen atom into a compound of formula (I) wherein R is a $C_1$-$C_6$ alkyl, and/or, if desired, by converting a compound of formula (I) into another compound of formula (I), and/or, if desired, by converting a compound of formula (I) into a pharmaceutically acceptable salt thereof.

The compounds of formula (I), wherein $R_1$ and $R_2$ are both methyl or both ethyl or both propyl, or, taken together with the nitrogen atom, may be the N-pyrrolidinyl or the N-piperidyl radical, have been already described in literature (Ermili A., Roma G., Gazz. Chim. Ital., 101, 269, 1971; Ermili A., Roma G., Balbi A., Gazz. Chim. Ital., 101, 651, 1971) without any reference, however, either to a possible therapeutical use or to a possible pharmaceutical formulation containing these compounds.

The reaction between the compound of general formula (II) and the compound of general formula (III) is preferably carried out in presence of a catalyst, preferably phosphorus oxychloride ($POCl_3$).

Generally, the intermediate of formula

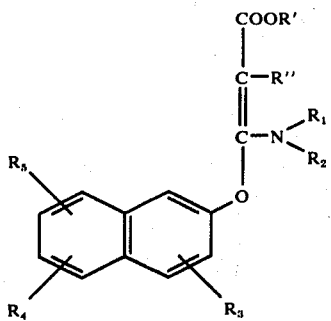

wherein $R_1$, $R_2$, $R_3$, $R_4$, $R_5$, R' and R'' are as defined hereabove, which is obtained by conducting the reaction in presence of phosphorus oxychloride, is not isolated.

The reaction between the compound of formula (II) and the compound of formula (III) is performed, at reflux temperature, in organic solvents, such as for example, dichloroethane and chloroform, and in an interval of time ranging, for instance, between an hour and ten hours. The other optional reactions are carried out with conventional methods. For example, the conversion of a compound of formula (I) wherein R is hydrogen into a compound of formula (I) wherein R is $C_1$–$C_6$ alkyl may be conducted by reaction with an alkylating agent, such as, for instance, an alkylhalide.

Hence, for instance, the conversion of a compound of formula (I) wherein one or more of $R_3$, $R_4$, $R_5$ is a nitrogroup, into a compound of formula (I) wherein one or more of $R_3$, $R_4$, $R_5$ is an aminogroup may be carried out by catalytic reduction, for example with palladium charcoal. As well as the optional conversions of a compound of formula (I) wherein one or more of $R_3$, $R_4$, $R_5$ is a hydroxy group into a compound of formula (I) wherein one or more of $R_3$, $R_4$, $R_5$ is an alkoxy group, or respectively, of a compound of formula (I) wherein one or more of $R_3$, $R_4$, $R_5$ is an alkoxy group into a compound of formula (I) wherein one or more of $R_3$, $R_4$, $R_5$ is a hydroxy group, may be carried out with conventional methods (such as for instance Williamson's reaction, or respectively treatment with pyridine hydrochloride or with a Lewis acid).

The compounds of formula (II) are known in literature, or respectively, may be prepared by means of methods known in literature.

The compounds of formula (III) may be for example obtained by reacting a compound of general formula:

wherein R' and R'' are as hereabove defined with an amine of formula

The reaction is preferably performed in a sealed tube at a temperature ranging for example between approximately 140° and 150° C and for an interval of time varying between approximately 34 and 38 hours.

1-oxo-1H-naphtho[2,1-b]pyran derivatives as well as the pharmaceutical compositions containing them, being the object of the present invention, are active on the central nervous system as antidepressive agents. The antidepressive activity of the compounds of the invention, evaluated in mice from the prevention of reserpine-induced blepharospasm and hypothermia, is shown in the following Table, where the antireserpine effect is indicated as $ED_{50}$ values, that is, doses able to prevent reserpine-induced blepharospasm and hypothermia by reducing symptoms of 50% if compared with the values obtainable in control animals.

TABLE

| Compound | Number of animals used (mice) | Anti-Reserpine Activity | |
|---|---|---|---|
| | | Blepharospasm $ED_{50}$ mg/kg/os | Hypothermia $ED_{50}$ mg/kg/os |
| 1-oxo-3-dimethyl= amino-1H-naphtho [2,1-b]pyran | 60 | 8.7 | 21 |
| 1-oxo-3-(N-me= thyl-N-ethyl) amino-1H-naphtho [2,1-b]pyran | 120 | 4 | 15 |

Reserpine was administered endoperitoneally at a dosage of 2.5 mg/kg, and the compounds tested were administered orally 30 minutes before administration of reserpine. Recording of blepharospasm (evaluated in scores according to the technique described by Rubin B. et al in J. Pharmacol. 120, 125, 1957) and measurement of body temperature (by means of a rectal thermocouple gavage) were taken an hour, and respectively, four hours after the administration of reserpine. In particular, the compounds object of the present invention not only allow to obtain a lower general toxicity in comparison with standard antidepressive agents, but also a lower cardiac toxicity as well as the lack of peripheral atropine effects.

The compounds of the present invention are preferably administered orally.

The results of the clinical tests in humans have confirmed the pharmacological data.

The dosage suitable for oral administration, for instance of 1-oxo-3-(N-methyl-N-ethyl)amino-1H-naphtho-[2,1-b]pyran, is preferably of 25-50 mg pro dose 2-4 times a day.

The pharmaceutical compositions containing the compounds of this invention are preferably tablets, pills or gelatine capsules which contain the active substance together with diluents, such as, for example, lactose, dextrose, sucrose, mannitol, sorbitol, cellulose; lubricants, for instance, silica, talc, stearic acid, magnesium or calcium stearate, and/or polyethylene glycols; or they may also contain binders, such as, for example, starches, gelatine, methylcellulose, carboxymethylcellulose, gum-arabic, tragacanth, polyvinylpyrrolidone; disintegrating agents, such as, for instance, starches, alginic acid, alginates, sodium carboxymethylamido, cellulose derivatives, effervescing mixtures; dyestuffs; sweeteners; wetting agents, such as, for instance, lecithin, polisorbates, laurylsulphates; and, in general, nontoxic and pharmacologically inactive substances used in pharmaceutical formulations. Said pharmaceutical preparations may be manufactured in known manner, for example, by means of mixing, granulating, tableting, dragee-making, or film-coating processes.

The following examples illustrate but do not limit the present invention.

EXAMPLE 1

POCl$_3$(11.5 g; 0.075 moles) was slowly added, ice-cooling, to N-methyl-N-ethylethoxycarbonylacetamide (9.52 g; 0.055 moles) in a round-bottomed, three-neck flask having a mechanical stirrer, a separatory funnel and a reflux condenser fitted with a calcium chloride tube. The mixture was left at room temperature for 40 minutes under stirring, then β-naphthol (7.2 g; 0.050 moles) suspended in symmetrical dichloroethane (40 ml) was added, and refluxed for 4 hours; after cooling at room temperature, a solution of CH$_3$COONa . 3H$_2$O (68g) in water (300 ml) was slowly added, then refluxed for two hours; the organic phase was subsequently separated and the alkaline waters extracted again with dichloroethane.

By evaporation of the solvent, a thick reddish oil was obtained from the collected extracts after washing with water: said oil was shaken with a mixture consisting of NaOH 2N and ethylether, then let rest in an open container.

After separation by filtration, washing with water, drying, crystallisation from ligroin, ethylether or benzene, 1-oxo-3-(N-methyl-N-ethyl)amino-1H-naphtho[2,1-b]pyran (5.8 g; m.p. 117°–118° C) is obtained.

N-methyl-N-ethylethoxycarbonylacetamide used as starting material was prepared as follows. A mixture consisting of diethyl malonate (60 g; 0.37 moles) and N-methyl-N-ethylamine (21.8 g; 0.37 moles) was heated at 150° C for 38 hours under stirring in a stainless-steel tube fitted with a hermetic seal. By fractioned distillation of the reaction product, N-methyl-N-ethylethoxycarbonylacetamide was obtained (35.5 g; b.p. ° C/mm Hg 76/0.09).

By proceeding in an analogous way, the other ethoxycarbonylacetamides used as starting materials for the preparation of the compounds described in the following examples, were obtained.

EXAMPLE 2

A mixture consisting of N,N-diisopropylethoxycarbonylacetamide (11.84 g; 0.055 moles; b.p. ° C/mm Hg 137–138/0.13), POCl$_3$ (11.5 g; 0.075 moles), β-naphthol (7.2 g; 0.050 moles), and dichlororethane (40 ml), obtained as previously described, was refluxed for 7 hours. After rest to room temperature, a solution of NaHCO$_3$ (42 g) in water (500 ml) was slowly added, then refluxed for 90 minutes: the organic phase was then separated and the alkaline waters were again extracted with dichloroethane. The collected extracts were firstly shaken twice with a warm solution of NaHCO$_3$ 10% (80 ml), then with three portions of NaOH N (each of 100 ml), finally washed with water. The thick dark oil obtained after evaporation of the solvent, treated with ethylether, allowed to separate, after crystallisation from ligroin, 1-oxo-3-diisopropylamino-1H-naphtho[2,1-b]pyran (3.1 g; m.p. 154°–155° C), as a crystalline white solid.

By proceeding in an analogous way, the following compounds were prepared:
1-oxo-3-methylamino-1H-naphtho[2,1-b]pyran;
1-oxo-3-ethylamino-1H-naphtho[2,1-b]pyran;
1-oxo-3-propylamino-1H-naphtho[2,1-b]pyran;
1-oxo-3-isopropylamino-1H-naphtho[2,1-b]pyran.

EXAMPLE 3

POCl$_3$ (11.5 g; 0.075 moles) was added slowly, ice-cooling, to N,N-diallylethoxycarbonylacetamide (11.61 g; 0.055 moles; b.p. ° C/mm Hg 94–95/0.13) in a round-bottomed, three-neck flask having a mechanical stirrer, a separatory funnel and a reflux condenser fitted with a calcium chloride tube. The mixture was left at room temperature for 45 minutes under stirring; then β-naphthol (7.2 g; 0.055 moles) suspended in symmetrical dichloroethane (40 ml) was added, and the mixture refluxed for 7 hours. After cooling, the mixture was treated with a concentrated aqueous solution containing NaHCO$_3$ (42 g), then boiled to reflux for 90 minutes; the solvent was separated and the aqueous phase extracted again with dichloroethane. The collected extracts were firstly shaken twice with a warm solution of NaHCO$_3$ 10% (80 ml), then with three portions of NaOH N (each of 100 ml), finally washed with water and dried up. The thick dark oil so obtained, after evaporation of the solvent, was taken up with little ethylether, to yield, after filtration and recrystallisation from acetone, 1-oxo-3-diallylamino-1H-naphtho[2,1-b]pyran (1.85g; m.p. 132°–133° C), as a crystalline white solid, practically pure.

After removal of ethylether, the residual oil, taken up with NaOH 2N (100 ml) and boiled to reflux for two hours and a half, still yielded 1-oxo-3-diallylamino-1H-naphtho[2,1-b]pyran (0.65 g. for a total of 2.50 g).

EXAMPLE 4

POCl$_3$ (11.5 g; 0.075 moles) was added slowly, ice-cooling, to N,N-diethylethoxycarbonylacetamide (10.3 g; 0.055 moles; b.p. ° C/mm Hg 132–133/0.15) in a round-bottomed, three-neck flask having a mechanic stirrer, a separatory funnel and a reflux condenser fitted with a calcium chloride tube. The mixture was left at room temperature for 40 minutes under stirring, then, after addition of 2-hydroxy-7-methoxynaphthalene (8.7 g; 0.050 moles) suspended in symmetrical dichloroethane (40 ml), the mixture was refluxed for 7 hours. After cooling to room temperature, a solution of NaHCO$_3$ (42 g) in water (500 ml) was slowly added to the mixture, then heated to reflux for 90 minutes. The organic phase was then separated, and the alkaline waters were extracted again with dichloroethane. The collected extracts were at first shaken twice with a warm solution of NaHCO$_3$ 10% (80 ml), then with three portions of NaOH N (each of 100 ml), and finally washed with water. After evaporation of the solvent, the so obtained dark oil was dissolved in boiling ligroin and fully bleached. The resulting precipitate, after concentration and recrystallisation from ethyl alcohol, was 1-oxo-3-diethylamino-9-methoxy-1H-naphtho[2,1-b]pyran (1.8 g; m.p. 122°–123° C).

EXAMPLE 5

POCl$_3$(11.5 g; 0.075 moles) was slowly added, ice-cooling, to N,N-diethylethoxycarbonylacetamide (10.3 g; 0.055 moles; b.p, ° C/mm Hg 132–133/0.13) in a round-bottomed, three-neck flask having a mechanical stirrer, a separatory funnel and a reflux condenser fitted with a calcium chloride tube. The mixture was then left at room temperature for 40 minutes under stirring, then, after addition of 2-hydroxy-3-methoxynaphthalene (8.7 g; 0.050 moles) suspended in symmetrical dichloroethane (40 ml), it was heated to reflux for four hours. After cooling to room temperature, a solution of NaHCO$_3$ (42 g) in water (500 ml) was slowly added to the mixture, which was then heated to reflux for 90 minutes. The organic phase was then separated and the alkaline waters were extracted again with dichloroethane. The collected extracts were at first shaken twice with a warm solution of NaHCO$_3$ 10% (100 ml), then with three portions of NaOH N (each of 100 ml), finally washed with water. After evaporation of the solvent, the dark oil so obtained was shaken for long with HCl (100 ml ; 1:1).

The soft yellowish mass so formed was separated and washed with water by decantation, then, after addition of acetone, and recrystallisation from absolute ethyl alcohol, yielded 1-oxo-3-diethylamino-5-methoxy-1H-naphtho[2,1-b]pyran . HCl (1.9 g; m.p. 204°–206° C). After mixing vigorously with a solution saturated with Na$_2$CO$_3$, and recrystallisation from benzene, 1-oxo-3-diethylamino-5-methoxy-1H-naphtho[2,1-b]pyran was obtained (1.5 g; m.p. 150°–151° C).

EXAMPLE 6

Tablets, each weighing 200 mg and containing 25 mg of the active substance were manufactured as follows:

| Composition (for 10,000 tablets): | |
|---|---|
| 1-oxo-3-dimethylamino-1H-naphtho[2,1-b]pyran | 250 g |
| lactose | 1,230 " |
| corn starch | 450 " |
| talc powder | 50 " |
| magnesium stearate | 20 " |

1-oxo-3-dimethylamino-1H-naphtho[2,1-b]pyran, lactose and half of the corn starch were mixed; the mixture was then forced through a sieve of 0.5 mm openings. Corn starch (30 g) was then suspended in warm water (300 ml). The resulting paste was used to granulate the powder mixture. The granules were dried, comminuted on a sieve of sieve size 1.4 mm, then the remaining quantity of starch, the talc and the magnesium stearate were added, carefully mixed and processed into tablets using punches of 8 mm diameter.

EXAMPLE 7

Tablets, each weighing 200 mg and containing 25 mg of the active substance were manufactured as follows:

| Composition (for 10,000 tablets): | |
|---|---|
| 1-oxo-3-(N-methyl-N-ethyl)amino-1H-naphtho[2,1-b]pyran | 250 g |
| lactose | 1,230 g |
| corn starch | 450 g |
| talc powder | 50 g |
| magnesium stearate | 20 g |

The tablets were prepared as described in Example 7.

We claim:
1. Method of treating depression in patients in need of such treatment, said method comprising orally administering to said patients an antidepressive therapeutically effective amount of a compound of the formula:

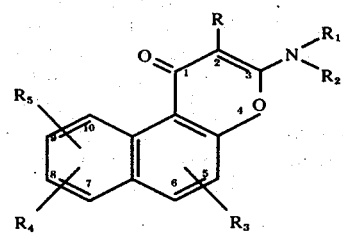

wherein R may be hydrogen, halogen or C$_1$–C$_6$ alkyl; each of the R$_3$, R$_4$ and R$_5$ groups, being the same or different, may be hydrogen, halogen, nitro, hydroxy, amino, C$_1$–C$_6$ alkyl, C$_1$–C$_6$ alkoxy or trifluoromethyl; each of the R$_1$ and R$_2$ groups, being the same or different, may be hydrogen, C$_1$–C$_6$ alkyl, C$_2$–C$_6$ alkenyl, or R$_1$ and R$_2$, taken together with the nitrogen atom, may form a monocyclic ring which may contain one or more other hetero atoms, or a physiologically acceptable salt thereof.

2. Method of claim 1, wherein said compound is 1-oxo-3-(N-methyl-N-ethyl)amino-1H-naphtho [2,1-b]pyran.

3. An antidepressive pharmaceutical composition comprising an effective amount of a compound of formula

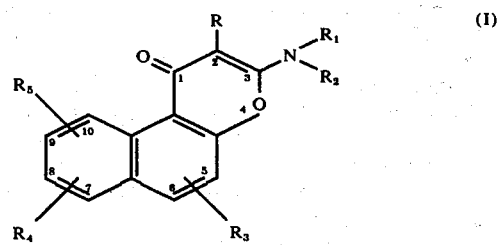

wherein R may be hydrogen, halogen or C$_1$–C$_6$ alkyl; each of the R$_3$, R$_4$ and R$_5$ groups, being the same or different, may be hydrogen, halogen, nitro, hydroxy, amino, C$_1$–C$_6$ alkyl, C$_1$–C$_6$ alkoxy or trifluoromethyl; each of the R$_1$ and R$_2$ groups, being the same or different, may be hydrogen, C$_1$–C$_6$ alkyl, C$_2$–C$_6$ alkenyl, or R$_1$ and R$_2$, taken together with the nitrogen atom, may form a monocyclic ring which may contain one or more other heteroatoms, or a physiologically acceptable salt thereof and a pharmaceutical acceptable carrier.

4. A pharmaceutical composition according to claim 3 suitable for oral administration, wherein said carrier is a pharmaceutically acceptable solid carrier.

5. Composition of claim 3, wherein said composition is in the form of a tablet, pill or capsule.

6. Composition of claim 5, wherein said tablet, pill or capsule contains from about 25 to about 50 mg of said compound.

7. Composition of claim 6, wherein said compound is 1-oxo-3-(N-methyl-N-ethyl)amino-1H-naphtho [2,1-b]pyran.

* * * * *